(12) United States Patent
Chang et al.

(10) Patent No.: US 8,673,587 B2
(45) Date of Patent: Mar. 18, 2014

(54) METHODS FOR IDENTIFYING ALLOSTERIC AND OTHER NOVEL ACYL-COENZYME A:CHOLESTEROL ACYLTRANSFERASE INHIBITORS

(75) Inventors: Ta-Yuan Chang, Etna, NH (US); Catherine C. Y. Chang, Etna, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/639,141

(22) PCT Filed: May 3, 2011

(86) PCT No.: PCT/US2011/034940
§ 371 (c)(1),
(2), (4) Date: Oct. 3, 2012

(87) PCT Pub. No.: WO2011/140047
PCT Pub. Date: Nov. 10, 2011

(65) Prior Publication Data
US 2013/0040327 A1 Feb. 14, 2013

Related U.S. Application Data

(60) Provisional application No. 61/331,188, filed on May 4, 2010.

(51) Int. Cl.
*C12Q 1/48* (2006.01)
(52) U.S. Cl.
USPC .......................................................... 435/15
(58) Field of Classification Search
None
See application file for complete search history.

(56) References Cited

U.S. PATENT DOCUMENTS

| | | | |
|---|---|---|---|
| 5,968,749 A | 10/1999 | Chang et al. | 435/6.12 |
| 2004/0115613 A1 | 6/2004 | Chang | 435/4 |
| 2004/0230050 A1 | 11/2004 | Cases et al. | 536/23.2 |
| 2008/0032897 A1 | 2/2008 | Chernoff | 506/4 |

OTHER PUBLICATIONS

Chang et al. "Acyl-Coenzyme A: Cholesterol Acyltransferases" American Journal of Physiology—Endocrinology and Metabolism 2009 vol. 297 (1) :E1-E9.
Deacon et al. "An Isoform-Selective, Small Molecule Inhibitor Targets the Autoregulatory Mechanism of p21—Activated Kinase" Chemistry & Biology 2008 vol. 15 (4) :322-331.
Hofmann, K. "A Superfamily of Membrane-Bound O-Acyltransferases with Implications for Wnt Signaling" Trends Biochemical Sciences 2000 vol. 25 (291) :111-112.
Liu, J. "Investigating ACAT Allosterism" Dartmouth College 2006 Dissertation Publication No. 3219707, abstract retrieved on-line Jul. 12, 2011 URL: http://gradworks.umi.com/32/19/3219707.html.
Liu et al. "Investigating the Allosterism of Acyl-CoA:Cholesterol Acyltransferase (ACAT) by Using Various Sterols: in vitro and Intact Cell Studies" Biochemical Journal 2005 vol. 391 (2):389-397.
Shi et al. "Comparison of Phosphatidylethanolamine and Phosphatidylcholine Vesicles Produced by Treating Cholate—Phospholipid Micelles with Cholestyramine" Biochimica et Biophysica Acta 1989 982:187-195.
Vourc'h et al. "$\Delta^5$-3$\beta$-Hydroxysteroid Acyl Transferase Activity in the Rat Brain" Steroids 1992 vol. 57 (5) :210-215.
Zhang et al. "Cholesterol Is Superior to 7-Ketocholesterol or 7$\alpha$-Hydroxycholesterol as an Allosteric Activator for Acyl-Coenzyme A:Cholesterol Acyltransferase 1" Journal of Biological Chemistry 2003 vol. 278 (13) :11642-11647.
International Search Report and Written Opinion from PCT/US2011/034940, Jul 26, 2011.
International Preliminary Report on Patentability from PCT/US2011/034940, Nov. 15, 2012.

*Primary Examiner* — Nashaat Nashed
(74) *Attorney, Agent, or Firm* — Licata & Tyrrell P.C.

(57) ABSTRACT

The present invention is a method for identifying compounds that are allosteric and/or other novel ACAT inhibitors that is based on the novel finding that pregnenolone is a substrate for ACAT; esterification of pregnenolone by ACAT is dramatically activated when cholesterol is present in the assay. The method comprises measuring the esterification of pregnenolone by ACAT under two different conditions: with cholesterol, or without cholesterol. This method can be used to test and categorize various candidate ACAT inhibitors as allosteric or other novel ACAT inhibitors, or it can be used in high-throughput screening for identifying such ACAT inhibitors.

10 Claims, 4 Drawing Sheets

METHODS FOR IDENTIFYING ALLOSTERIC AND OTHER NOVEL ACYL-COENZYME A:CHOLESTEROL ACYLTRANSFERASE INHIBITORS

This application is a U.S. National Stage Application of PCT/US2011/034940 filed May 3, 2011 and claims the benefit of priority of U.S. Provisional Application No. 61/331,188, filed May 4, 2010, the contents of each of which is are incorporated herein by reference in their entirety.

This invention was made with government support under Grant No. R01HL060306 awarded by the National Institutes of Health. The government has certain rights in the invention.

BACKGROUND OF THE INVENTION

Acyl-coenzyme A:cholesterol acyltransferase (ACAT) converts free cholesterol to cholesterol ester, and is one of the key enzymes in cellular cholesterol metabolism. The first ACAT gene (Acat1, also named Soat1) was identified in 1993 (Chang et al. 1993. *J. Biol. Chem.* 268:20747-20755). The ACAT enzyme family includes ACAT1, ACAT2 (Oelkers et al. 1998. *J. Biol. Chem.* 273:26765-26771), and acyl-coenzyme A:diacylglycerol acyltransferase 1 (DGAT1) (Buhman et al. 2000. *Biochim. Biophys. Acta* 1529:142-154). These enzymes are founding members of the membrane-bound O-acyltransferase enzyme family (MBOAT). MBOATs are multi-span membrane proteins that utilize long-chain or medium-chain fatty acyl-coenzyme A and a hydrophobic substance as their substrates (Hofmann, K. 2000. *Trends Biochem. Sci.* 25:111-112). Additional MBOATs include ghrelin octanoyl-coenzyme A acyltransferase (Yang et al. 2008. *Cell* 132:387-396) and lysophospholipid acyltransferases (LPATs; Shindou, H. and T. Shimizu. 2009. *J. Biol. Chem.* 284:1-5). See also, Chang C. Y. et al. 2011. *Front. Biol.* DOI 10.1007/s11515-011-1149-z.

Research on the therapeutic utility of ACAT1 and ACAT2 has focused on these enzymes as potential drug targets for treating dyslipidemia and atherosclerosis (Chang et al. 2009. *Am. J. Physiol.* 297:E1-E9). In addition, recent work has identified ACAT1 as a potential therapeutic target for treatment of Alzheimer's disease (AD) (Bryleva et al. 2010. *Proc. Natl. Acad. Sci.* 107:3081-3086).

Whether ACAT inhibitors may serve as effective anti-atherosclerosis drugs is under debate (Leon et al. 2005. *Pharm. Res.* 22:1578-1588; Feng et al. 2003. *Nat. Cell Biol.* 5:781-792; Nissen et al. 2006. *NEJM* 354:1253-1263; Rudel, L. L. and R. V. J. Farese. 2006. *NEJM* 354:2616-2617; Chang et al. 2006. *Acta Biochim. Biophys. Sin.* 38:151-156; Terasaka et al. 2007. *Atherosclerosis* 190:239-247; Meuwese et al. 2009. *JAMA* 301:1131-1139; Parini et al. 2009. *JAMA* 302:255; Dimmitt, S. and G. Watts. 2009. *JAMA* 302:255-256). Almost all of the ACAT inhibitors available to date were designed based on initial research from the 1980's and 1990's. The compounds were identified by using conventional biochemical assays based on the ability to inhibit ACAT activity in vitro. In vitro assays, for example, monitor levels of enzyme activity by measuring formation of radiolabeled cholesteryl oleate in microsomal fractions of mammalian cells (e.g., Erickson et al. 1980 *J. Lipid Res.* 930-941).

In studies using animal models for AD, the ACAT inhibitor CP113818 was shown to inhibit the processing of both human amyloid precursor protein (APP) and mouse APP; a different ACAT inhibitor CI1011 decreased the mature/immature ratio of human APP (Huttune et al. 2009. *FASEB J* 23:3819-3828). In contrast, Bryleva et al. (2010. *Proc. Natl. Acad. Sci.* 107:3081-3086) showed that in a similar mouse model for AD, ACAT1 gene knock out (Acat1$^{-/-}$) was associated with a decrease in full-length human APP protein content; however, there was no effect on mouse APP at any level, and no alteration in the ratio of mature human APP/immature human APP. In contrast to these effects in knockout mice (Acat1$^{-/-}$), CP113818 did not cause a reduction in full-length human APP content (Hutter-Paier et al. 2004. *Neuron* 44:227-238). The apparent discrepancy in results raises questions about the specificity of the ACAT inhibitors employed by various investigators. Although CP113818, CI1011 and other structurally related compounds are designated as ACAT inhibitors, they may also inhibit other enzymes in the MBOAT family. For instance, when fed to animals, CI1011 reduces the VLDL-triglyceride content, presumably due to its ability to inhibit DGAT1 in addition to inhibiting ACAT (Llayerias et al. 2003. *Cardiovasc. Drug Rev.* 21:33-50). Another ACAT inhibitor, CI976, widely used to block cholesteryl ester formation in experimental atherosclerosis research (Bocan et al. 1991. *Arterioscler. Thromb.* 11:1830-1843), has been shown to inhibit a unique, lysohpospholipid acyltransferase (LPAT; Brown et al. 2008. *Traffic* 9:786-797).

An additional concern regarding currently available ACAT inhibitors is that many ACAT inhibitors are hydrophobic, membrane active molecules (Homan, R. and K. L. Hamelehle 2001. *J. Pharm. Sci.* 90:1859-1867). The hydrophobicity of the ACAT inhibitors may enable these compounds to have easier access to the active sites of ACAT/MBOAT, which are often buried within the membrane bilayer (Chang et al. 2009. *Am. J. Physiol.* 297:E1-E9). An undesirable property of these membrane-active compounds is that in intact cells, these compounds may partition into membranes at relatively high concentration and perturb membrane properties in a nonspecific manner. Thus, the currently available ACAT inhibitors may cause membrane deformations in neurons and in other cell types. Novel ACAT1 and ACAT2 inhibitors are sought that have increased specificity and novel binding properties.

DESCRIPTION OF THE DRAWINGS

FIG. 2 depicts substrate saturation curves for pregnenolone, dihydroepiandrosterone (DHEA), and estradiol (E2) with or without cholesterol. ACAT1 was the enzyme source.

µM pregnenolone. Results shown are representative of two separate experiments; error bars represent deviation between duplicates.

Figure 4A:
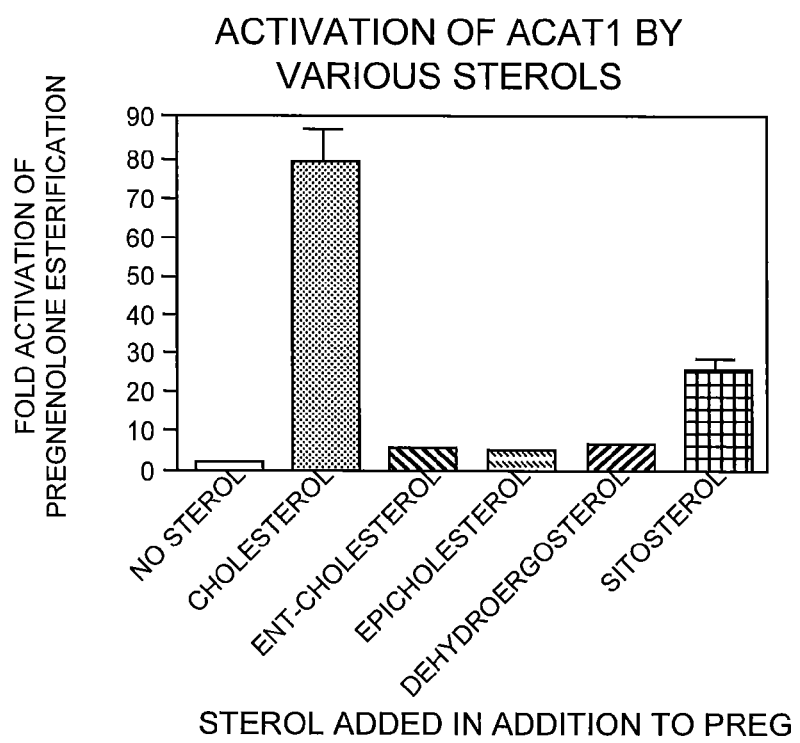
Figure 4B:
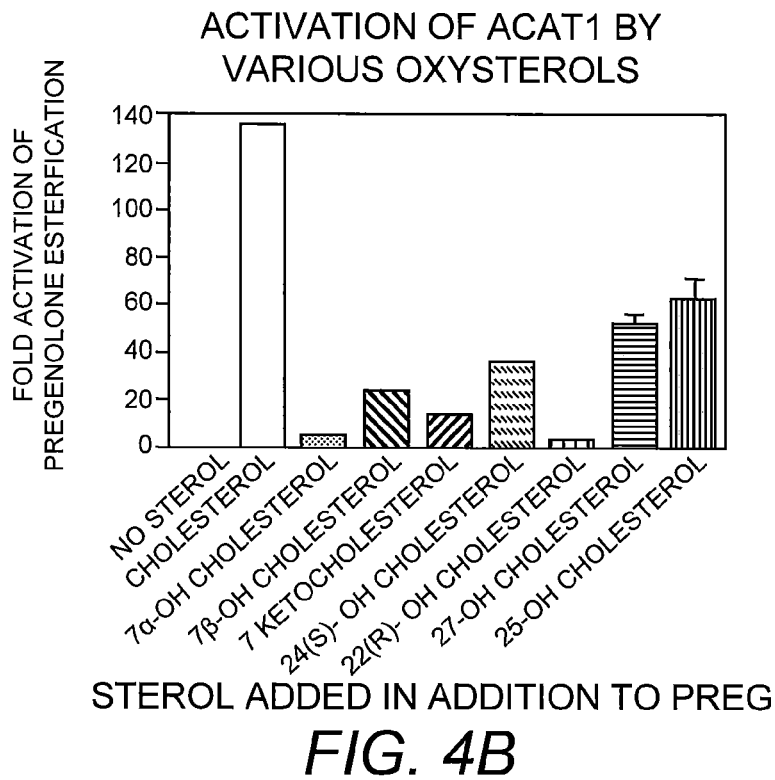
Figure 4C:
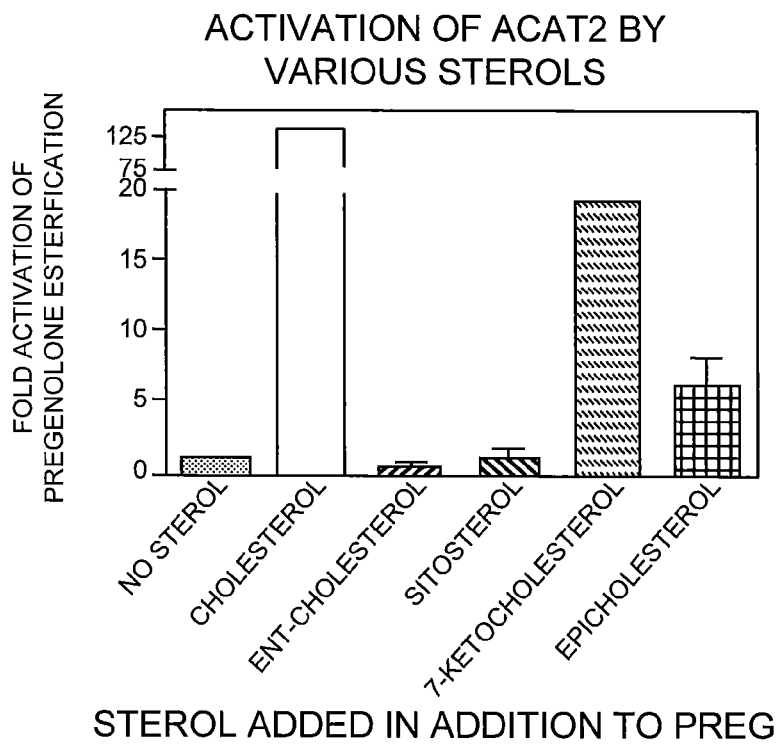

FIG. 4 depicts the results of experiments investigating the activation of pregnenolone esterification by various sterols. ACAT1 was used as the enzyme source in FIG. 4A and FIG. 4B, whereas ACAT2 was used as the enzyme source in FIG. 4C. In all experiments, 1 µM [$^3$H]-pregnenolone (specific activity 20 Ci/mmol) was tested in micelles in the absence or presence of 0.32 mM of various sterols as listed.

SUMMARY OF THE INVENTION

An object of the present invention is a method of identifying an allosteric acyl-coenzyme A: cholesterol acyltransferase (ACAT) inhibitor which includes a) determining a level of inhibition of pregnenolone esterification by ACAT in vitro in the presence of cholesterol for a candidate compound; b) determining a level of inhibition of pregnenolone esterification by ACAT in vitro without the presence of cholesterol for the compound; and c) comparing the level of inhibition of pregnenolone esterification in the presence of cholesterol with the level of inhibition of pregnenolone esterification without the presence of cholesterol, wherein the candidate compound is identified as an allosteric ACAT inhibitor if it inhibits pregnenolone esterification by ACAT in the presence of cholesterol but does not inhibit pregnenolone esterification by ACAT without the presence of cholesterol.

Another object of the present invention is a method of identifying a novel ACAT inhibitor which includes a) determining a level of inhibition of pregnenolone esterification by ACAT in vitro in the presence of cholesterol for a candidate compound; b) determining a level of inhibition of pregnenolone esterification by ACAT in vitro without the presence of cholesterol for the compound; and c) comparing the level of inhibition of pregnenolone esterification in the presence of cholesterol with the level of inhibition of pregnenolone esterification without the presence of cholesterol, wherein the candidate compound is identified as a novel ACAT inhibitor if it inhibits pregnenolone esterification by ACAT without the presence of cholesterol.

In another embodiment, the present invention identifies allosteric and novel ACAT inhibitors that are ACAT1 inhibitors or ACAT2 inhibitors.

Another object of the present invention is a method wherein the esterification of pregnenolone by ACAT in vitro is determined in an assay that includes a histidine-tagged recombinant human ACAT1 or a histidine-tagged human ACAT2 enzyme preparation purified by nickel column chromatography. In yet another embodiment, the esterification of pregnenolone by ACAT in vitro is tested in a mixed micelle mixture which further comprises a detergent, phosphatidylcholine, a radiolabelled pregnenolone, and fatty acyl-coenzyme A. The methods of the present invention can also involve use of multi-well microtiter plates for high throughput screening to identify allosteric or novel ACAT inhibitors.

DETAILED DESCRIPTION OF THE INVENTION

There are two different types of enzyme inhibitors for certain enzymes, termed "orthosteric" enzyme inhibitors and "allosteric" enzyme inhibitors (Drahl, C. 2009. *Chem. Eng. News* 87:12-14). Conventional enzyme inhibitors are orthosteric inhibitors, which are compounds that inhibit the active, or catalytic, site or sites within the protein. In contrast, allosteric enzyme inhibitors are compounds that bind to novel, non-catalytic site or sites within the protein, sites often referred to as regulatory sites. Members of a given enzyme/protein family may share similar substrates and similar catalytic mechanisms. Yet, their allosteric sites may be less evolutionarily conserved than the orthosteric sites. These characteristics may offer allosteric inhibitors advantages such as avoiding or minimizing drug overdose effects or lessening side effects of drugs.

Both ACAT1 and ACAT2 utilize cholesterol and long-chain fatty acyl-coenzyme A as their normal enzyme substrates, and both have been shown to be allosteric enzymes (Chang et al. 2009. *Am. J. Physiol.* 297:B1-9). The interaction of the substrate cholesterol with the ACAT enzymes (both ACAT1 and ACAT2) results in a sigmoidal-shaped curve for enzyme activity. Cholesterol is superior to oxysterols, as well as any other sterol, as an activator for ACAT. Upon activation by cholesterol, ACAT enzyme activity is increased, and the interaction of the enzyme with a variety of substrates, such as sterols with a 3-β-OH configuration, is increased (Zhang et al. 2003. *J. Biol. Chem.* 278:11642-11647; Liu et al. 2005. *Biochem. J.* 391:389-397). Although there is currently no structural model for either ACAT1 or ACAT2, using a series of sterol analogs, results of biochemical studies indicate the presence of a sterol substrate site and a sterol activator site in ACAT1 and in ACAT2; the structural elements for the ACAT substrate site and the ACAT activator site are distinct. For example, studies have shown that the stereochemistry of the 3-hydroxy group at steroid ring B in ACAT substrates is a critical structural feature for any sterol to serve as a substrate, but is less critical for sterol-dependent activation of ACAT (Liu et al. 2005. *Biochem. J.* 391:389-397)

Until the findings of the present invention, no ACAT substrate has been identified that only serves as a substrate, not as a sterol activator. It has now been found that pregnelonone fulfills the criterion for such a sterol. When cholesterol is present in abundance, pregnenolone, a distant structural analog of cholesterol, becomes an efficient substrate for ACAT1 or ACAT2. However, when cholesterol is absent, pregnenolone is an extremely poor ACAT substrate. Thus, it has been demonstrated for the first time that 1) pregnenolone is an ACAT substrate; 2) unlike many other analogs of cholesterol previously tested, pregnenolone can serve as an ACAT substrate but cannot act as an activator of ACAT1/ACAT2; and 3) when pregnenolone is used as the substrate for ACAT, allosteric activation of ACAT by cholesterol (or other appropriate sterols) is needed in order for it to function efficiently as a sterol acyltransferase. Thus, a method has been developed for identifying novel ACAT inhibitors, compounds that are allosteric inhibitors of ACAT, both ACAT1 and ACAT2. The allosteric inhibitor can act through various mechanisms. For example, it may compete against cholesterol for binding at the allosteric activator site(s). Alternatively, it may bind to the enzyme at separate, novel site(s) to prevent conformational changes triggered by cholesterol binding to the enzyme's activator site. Such allosteric inhibitors would be desired as they are capable of inhibiting ACAT enzyme activity by binding the enzyme at non-catalytic, regulatory site(s); these inhibitors may not be accompanied by unwanted side effects that are seen with conventional, orthosteric ACAT inhibitors. The method of the present invention will also allow one of skill in the art to identify novel ACAT inhibitors that are not simply allosteric inhibitors by identifying compounds that inhibit pregnenolone esterification independent of cholesterol activation.

There have been no previous reports of allosteric ACAT inhibitors in part due to the lack of an appropriate assay capable of clearly distinguishing the ACAT inhibitor as an allosteric inhibitor as compared to an orthosteric inhibitor.

The present invention is a simple, novel, and extremely sensitive method that can be used to identify allosteric ACAT1 or ACAT2 inhibitors, as well as other novel ACAT1 and ACAT2 inhibitors. The significance of this invention can be illustrated in two ways. First, a variety of conventional ACAT enzyme assays in vitro or in intact cells are available in the art, and would be used as a first step to identify small molecules as candidate ACAT inhibitors, ones that may or may not have allosteric inhibitor activity. Once a given candidate ACAT inhibitor compound is identified using currently available ACAT enzyme activity assays, the candidate inhibitor would be tested using the method of the present invention as an allosteric ACAT inhibitor. The candidate compound is identified as an allosteric ACAT inhibitor if it inhibits pregnenolone esterification in the presence of cholesterol but does not inhibit basal pregnenolone esterification in the absence of cholesterol. The method of the present invention is also a method of identifying novel ACAT inhibitor if the compound inhibits pregnenolone esterification without cholesterol present. This is because the present invention has shown for the first time that pregnenolone esterification is a substrate for ACAT, making compounds that act through this mechanism novel ACAT inhibitors. Second, the method of the present invention can be conducted in multi-well microtiter plates and used in high-throughput screening to identify allosteric ACAT inhibitors, as well as other novel ACAT inhibitors, without prior knowledge of the compound.

The method of the present invention was developed in experiments using a mixed micelle enzyme assay system. In this system, when radiolabeled pregnenolone is used as the substrate, cholesterol added in the assay mixture dramatically activated the ability of ACAT1 or ACAT2 to esterify pregnenolone. For either enzyme, ACAT1 or ACAT2, cholesterol has been shown to activate pregnenolone esterification activity by more than 100-fold. A candidate ACAT inhibitor is an allosteric inhibitor if it is shown in the method of the present invention to inhibit cholesterol-dependent pregnenolone esterification but not to inhibit the basal pregnenolone esterification when cholesterol is absent in the assay mixture. If the compound inhibits pregnenolone esterification with or without cholesterol present, then the compound is also identified as a novel pregnenolone esterification inhibitor. In the assay system of the present invention, the source of ACAT was histidine-tagged recombinant human ACAT1 or human ACAT2, stably expressed in Chinese hamster ovary (CHO) cells that lack endogenous ACAT activity. However, one of skill in the art could employ other suitable mammalian cell systems as needed. The enzyme preparations used in the present method were partially purified through the use of nickel column chromatography, as described previously (Liu et al. 2005. *Biochem. J.* 391:389-397), using cells that stably expressing histidine-tagged recombinant human ACAT1 or human ACAT2 as the enzyme source.

Figure 1A:
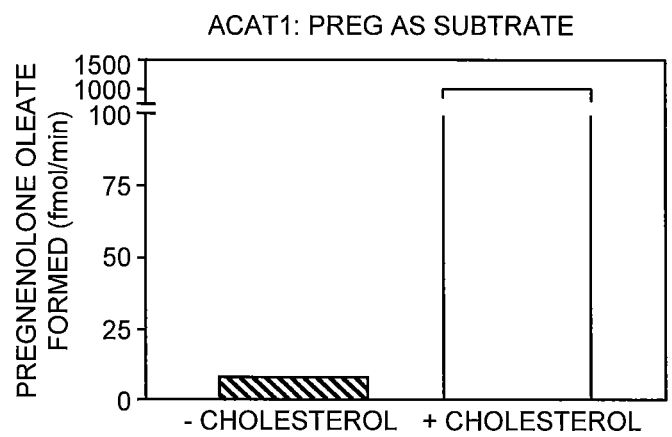
FIG. 1 depicts the esterification of pregnenolone and dihydroepiandrosterone (DHEA) in the presence or absence of cholesterol by ACAT in vitro. ACAT1 or ACAT2, purified through nickel column chromatography, was used as the enzyme source. In these experiments, 1 µM [$^3$H]-pregnenolone (specific activity 20 Ci/mmol) or 1 µM [$^3$H]-DHEA (specific activity 40 Ci/mmol) was incubated with micelles with or without 0.32 mM cholesterol. Results shown are representative of two separate experiments; error bars represent deviation between duplicates.
Figure 1B:
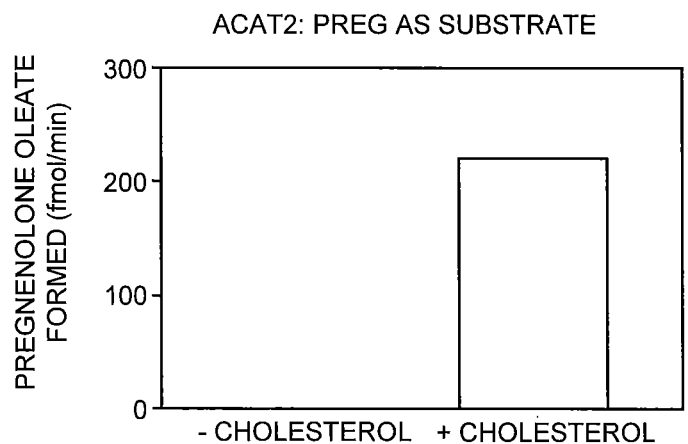
Figure 1C:
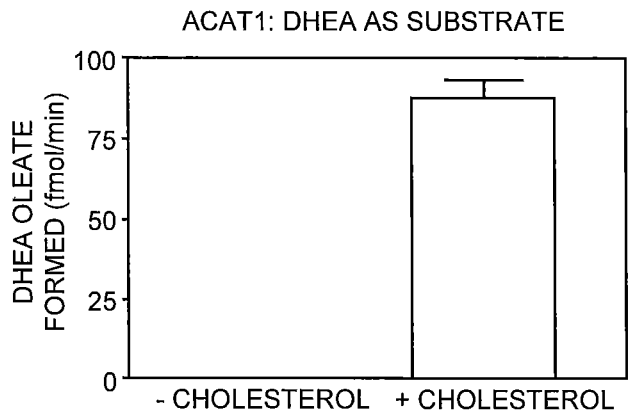

In developing the method of the present invention, a series of experiments was performed. Pregnenolone is one compound that contains the classical A, B, C, D steroid rings as well as a 3 beta-OH moiety. Based on its structure, pregnenolone may be an ACAT substrate. However, this possibility had not previously been tested experimentally. In the present invention, the activity of pregnenolone was tested by using radiolabeled pregnenolone ([$^3$H]-pregnenolone) in a mixed micelle enzyme assay mixture that contained the detergent taurocholate (or CHAPS), phosphatidylcholine, and oleyl-coenzyme A bound to bovine serum albumin (BSA). The enzyme used was histidine-tagged human ACAT1 or human ACAT2. The esterification of pregnenolone (i.e., formation of pregnenolone oleate) was monitored by performing lipid extraction to isolate [$^3$H]-pregnenolone oleate and [$^3$H]-pregnenolone. [$^3$H]-pregnenolone oleate was then separated from [$^3$H]-pregnenolone by using conventional thin-layer chromatography. Levels of [$^3$H]-pregnenolone oleate formed was measured using a scintillation counter. When pregnenolone was added to the assay mixture in the absence of cholesterol, pregnenolone was shown to be a very poor substrate for ACAT1 (FIG. 1A) and ACAT2 (FIG. 1B). However, in the presence of excess cholesterol (0.32 mM), pregnenolone became a much better substrate for ACAT1 as well as ACAT2. DHEA, an obligatory biosynthetic intermediate between pregnenolone and various sex steroid hormones, is the only other steroid that possesses the same classical A, B, C, D steroid ring structure as well as a 3 beta-OH moiety. Thus, using ACAT1 as the enzyme source, the esterification of DHEA was examined (FIG. 1C). In the absence of cholesterol in vitro, DHEA did not exhibit ACAT substrate activity, whereas in the presence of cholesterol (0.32 mM), DHEA exhibited significant substrate activity, similar to the effects seen with pregnenolone. Comparing the results obtained with pregnenolone versus DHEA, however (FIGS. 1A and 1C), revealed that pregnenolone showed superior activity as an ACAT substrate as compared to DHEA.

Figure 2A:
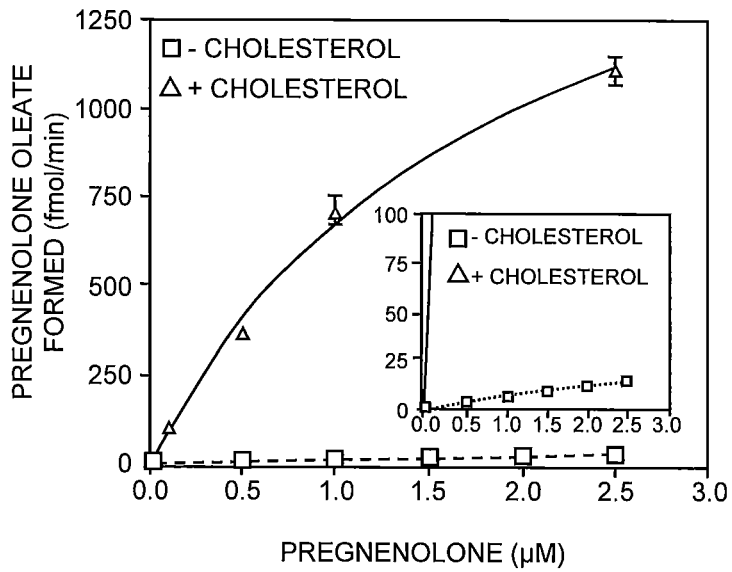
In FIG. 2A, [$^3$H]-pregnenolone (specific activity 20 Ci/mmol) was added in mixed micelles with or without 0.32 mM cholesterol. The inset shows a portion of the result at a higher magnification.
Figure 2B:
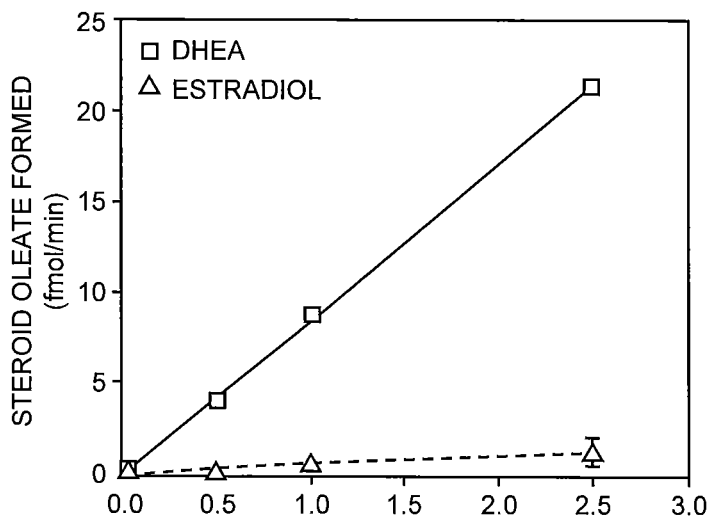
In FIG. 2B, [$^3$H]-DHEA (specific activity 40 Ci/mmol) or [3H]-E2 (specific activity 42 Ci/mmol) was added to mixed micelles with or without 0.32 mM cholesterol. Results shown are representative of two separate experiments; error bars represent deviation between duplicates.

A pregnenolone substrate saturation curve was then constructed, with or without addition of cholesterol to the assay mixture, using ACAT1 as the enzyme source (FIG. 2A). Results showed that cholesterol activated pregnenolone esterification by more than 100-fold. Analysis revealed that the cholesterol-dependent activation was associated with a reduction in the apparent $K_m$ for pregnenolone, as well as a very large increase in the $V_{max}$ for production of pregnenolone ester. Without cholesterol present in vitro, the $K_m$ for pregnenolone is too high to be measurable; with cholesterol present in vitro (added at 0.32 mM), the apparent $K_m$ for pregnenolone is about 1.2 µM. Then, a DHEA substrate saturation curve was constructed, with cholesterol present. Results showed (FIG. 2B) that the apparent $K_m$ for DHEA is too high to be measurable; additional result showed that estradiol (E2) is not an ACAT1 substrate. Earlier work by others had identified the presence of a form of acyltransferase in rat brain microsomes that esterified several steroids including, pregnenolone and estradiol; however, the activity of that acyltransferase was higher in the presence of estradiol as a substrate as compared to pregnenolone, and was inactive in the presence of cholesterol as a substrate (Vourc'h et al. 1992. *Steroids* 5:210-215). The current results demonstrated that ACAT1 is distinct from the enzyme activity reported by Vourc'h et al. (1992. *Steroids* 5:210-215).

Figure 3:
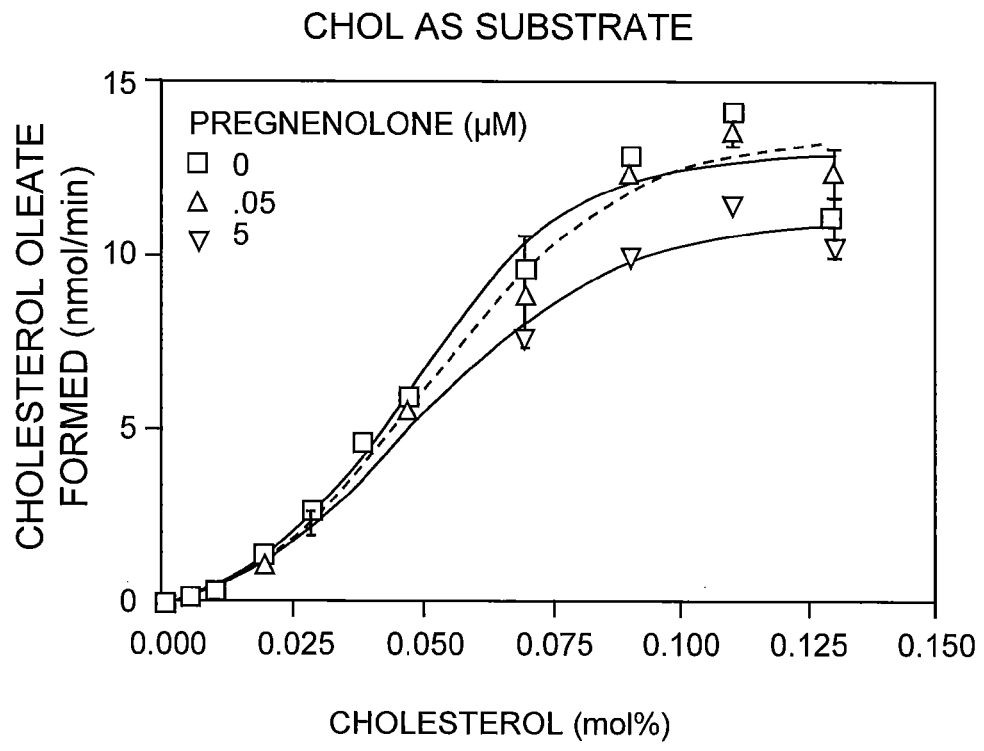
FIG. 3 depicts the effect of pregnenolone on cholesterol esterification in vitro. ACAT1 was the enzyme source. [$^3$H]-oleoyl-CoA/BSA was the labeled substrate. Cholesterol was incubated in mixed micelles in the presence of 0, 0.05, or 5

The effects of pregnenolone on the cholesterol substrate saturation curve were then investigated, again using ACAT1 as the enzyme source (FIG. 3). Results showed that pregnenolone added at a high concentration (5 µM; a concentration approximately four times the apparent $K_m$ value for pregnenolone) only slightly inhibited cholesterol esterification (10-15% inhibition). The inhibitory effect of pregnenolone was linked to a decrease in the $V_{max}$ for cholesterol esterification, not to any effect on the apparent $K_m$ for cholesterol, which is approximately 0.3 mM.

The pregnenolone esterification assay provides a very sensitive method to monitor the ability of various sterols as enzyme activators. Further experiments were performed to examine the effect of adding various non-oxysterols, at a concentration of 0.32 mM, on pregnenolone esterification in vitro, with ACAT1 as the enzyme source. As shown in FIG. 4A, among the sterols tested, cholesterol provided the maximal activation of ACAT1 and resulted in significant levels of pregnenolone esterification in vitro. Sitosterol, a plant sterol, also activated pregnenolone esterification, although not as efficiently as cholesterol. Epi-cholesterol (a cholesterol analog with a 3 alpha-OH moiety at ring A), enantiomeric (ent-) cholesterol (the mirror image of cholesterol), and dehydroergosterol (a fluorescent cholesterol analog) also activated pregnenolone esterification, although much less efficiently than sitosterol. In contrast to sitosterol, it was previously shown that none of these other three sterols is an ACAT1 substrate ((Liu et al. 2005. *Biochem. J.* 391:389-397). Next, the effects of various oxysterols (at concentration 0.32 mM) on pregnenolone esterification were tested. Results showed that essentially all the oxysterols tested activated pregnenolone esterification, but at varying degrees (FIG. 4B). The oxysterols that produced the least activation were 22R-hydroxy-cholesterol a biosynthetic intermediate during the conversion of cholesterol to pregnenolone, and 7-alpha-OH-cholesterol, the first biosynthetic intermediate from cholesterol in the bile acid biosynthesis pathway.

When ACAT2 was the enzyme source, it was found that cholesterol also provided maximal activation of pregnenolone esterification, followed by 7-ketocholesterol, an auto-oxidation product of cholesterol (FIG. 4C). Unlike the results seen when ACAT1 was used, the plant sterol sitosterol only slightly activated ACAT2 esterification of pregnenolone. These results indicated that the mechanisms of sterol-dependent activation of ACAT1 and ACAT2 are similar, but not identical.

Considered together, the results of the experiments with ACAT enzymes showed that pregnenolone is a substrate for ACAT1 and ACAT2 in vitro. For ACAT1, when cholesterol is present, the substrate saturation curve of pregnenolone is hyperbolic, with an estimated $K_m$ 600-fold lower than that of cholesterol. The presence of pregnenolone only slightly inhibited cholesterol esterification. Various oxysterols markedly activated pregnenolone esterification in vitro. Based on these collective results, a model for ACAT1 allosterism was developed. The model contains the following features: 1) ACAT1 is a homotetramer, although functionally it may act as a dimer. Within each dimer, the enzyme may contain two identical sterol substrate sites, and no more than two sterol activator sites. 2) The sterol substrate sites preferentially bind pregnenolone, although they can also bind a variety of sterols with 3-beta OH in ring A (e.g., cholesterol, sitosterol, and oxysterols). The binding between the sterol substrate site and the steroid is mainly stereospecific. This site may not be able to bind ent-cholesterol, or epi-cholesterol, or dehydroergosterol. The sterol activator site or sites, however, prefers to bind cholesterol, although it can also bind a variety of other sterols such as sitosterol, oxysterols, ent-cholesterol, and dehydroergosterol; this activator site may not bind pregnenolone or DHEA. Since the sterols interact biophysically with membrane phospholipids in a manner similar to that of cholesterol, the binding between the activator site and the steroid may involve the biophysical properties as well as the stereospecific structures of the sterol. 3) When only pregnenolone is present, pregnenolone may bind to the substrate sites with lower affinity. Since pregnenolone cannot activate the enzyme, binding of pregnenolone at these sites fails to trigger appropriate conformational changes, and the enzyme can only catalyze pregnenolone esterification at a very low, minimal rate. 4) When pregnenolone and cholesterol are both present, binding of cholesterol at the activator site or sites causes conformational changes, enabling the enzyme to bind pregnenolone and catalyze the reaction much more efficiently. Various oxysterols, sitosterol, or ent-cholesterol, may partially substitute for cholesterol at the activator site. However, neither pregnenolone nor DHEA may bind the activator site (presumably due to limited size of the side-chain at ring D). Cholesterol binding at the activator site may also allow the enzyme to bind and esterify cholesterol at the substrate sites more efficiently. 5) When oxysterol and cholesterol are both present, cholesterol binds to the activator site, causing conformational changes that enable the enzyme to bind and esterify oxysterol, and possibly also cholesterol, at the substrate site more efficiently.

Thus, the data described herein provided the basis for design of the method of the present invention. The present invention is a method for identifying allosteric ACAT inhibitors which includes the steps of determining a level of inhibition of pregnenolone esterification by ACAT in vitro in the presence of cholesterol for a candidate compound; determining a level of inhibition of pregnenolone esterification by ACAT in vitro without the presence of cholesterol for the compound; and comparing the level of inhibition of pregnenolone esterification in the presence of cholesterol with the level of inhibition of pregnenolone esterification without the presence of cholesterol, wherein the candidate compound is identified as an allosteric ACAT inhibitor if it inhibits pregnenolone esterification by ACAT in the presence of cholesterol but does not inhibit pregnenolone esterification by ACAT without the presence of cholesterol. The allosteric inhibitors identified by the method of the present invention may act in various manners; for instances, they may compete against cholesterol for binding at the allosteric activator site(s), and/or may bind to the enzyme at other novel site(s) to prevent conformational change(s) triggered by cholesterol's binding at the activator site. In a similar method, the present invention is a method for identifying novel ACAT inhibitors which comprises determining a level of inhibition of pregnenolone esterification by ACAT in vitro in the presence of cholesterol for a candidate compound; determining a level of inhibition of pregnenolone esterification by ACAT in vitro without the presence of cholesterol for the compound; and comparing the level of inhibition of pregnenolone esterification in the presence of cholesterol with the level of inhibition of pregnenolone esterification without the presence of cholesterol, wherein the candidate compound is identified as a novel ACAT inhibitor if it inhibits pregnenolone esterification by ACAT without the presence of cholesterol. Such novel ACAT inhibitors may inhibit binding between ACAT and pregnenolone or may act by some otherwise unidentified mechanism. In a preferred embodiment, the ACAT inhibitors are ACAT1 or ACAT2 inhibitors. In yet another embodiment, the esterification of pregnenolone by ACAT in vitro is determined in an assay that comprises a histidine-tagged recombinant human ACAT1 or a histidine-tagged human ACAT2 enzyme preparation purified by nickel column chromatography. The method may also be one wherein the esterification of pregnenolone by ACAT in vitro is tested in a mixed micelle mixture which further includes a detergent, phosphatidylcholine, a radiolabelled pregnenolone, and fatty acyl-coenzyme A. The method may also be adapted to use multi-well microtiter plates for high throughput screening to identify allosteric and other novel ACAT inhibitors.

One of skill in the art would understand that tests for determining inhibition of ACAT activity in vitro would include use of a variety of known assays described in the art. These assays could include those described in Chang et al. (1998. *J. Biol. Chem.* 273:35132-35141), Cadigan et al. (1988. *J. Biol. Chem.* 263:274-282), U.S. Pat. No. 5,834,283, U.S. Pat. No. 5,968,749, and Lada et al. (2004. *J. Lipid Res.* 45:378-386).

It should also be understood that one of skill in the art may find it desirable to adapt the method of the present invention for high-throughput screening of large groups of candidate compounds. Therefore, in another embodiment, the assay system described above is adapted to a high-throughput format such that it is performed in individual wells of multi-well (96 well or 384 well) microtiter plates, based on methods similar to what has been reported by others (Kristie et al. 2006. *Anal. Biochem.* 358: 266-272). When assayed in microtiter plates, the method of the present invention can be used as a method for primary high-throughput screen to identify allosteric ACAT inhibitors without any prior knowledge of the activity profile of the compound.

The following non-limiting examples are provided to further illustrate the present invention.

Example 1

Recombinant ACAT Expression in CHO Cells

A fragment of the ACAT gene was generated containing an ATG translation initiation codon, codons for a 6-histidine tag that functions as a metal binding domain, a T7 tag that serves as a transcript stabilizing sequence from gene 10 of phage T7, and an enterokinase cleavage recognition sequence (a total of 40 amino acids). This construct (originally designed by Invitrogen for baculovirus transfer vector pBLUEBACHIS) was ligated to the N terminus of hACAT-1 cDNA (nucleotide residues 1397-3046, a total of 550 amino acids, with the first methionine (ATG) converted to leucine (CTA) by site-specific mutagenesis). This entire fragment was then ligated into the expression vector pcDNA3 (Invitrogen). Using a modified calcium phosphate-DNA co-precipitation method (Hasan et al. 1991. *Somat. Cell Mol. Genet.* 17:513-517), or other method, the plasmid was transfected into an ACAT-deficient cell line, AC29, that lacks endogenous ACAT message and protein. One day after transfection, cells were selected for G-418 resistance by including 500 mg/ml G-418 in growth medium for 1 week. The G-418 resistant colonies were examined for their cytoplasmic cholesteryl ester lipid droplet content by microscopic examination. The clones that scored positive for cytoplasmic lipid droplets were approximately 5% of the total G-418 resistant clones; they were isolated with cloning rings and recloned by dilution. In this manner, a stable clone expressing high ACAT activity in vitro and in hACAT protein content was isolated. To maintain clonal purity, cloned HisACAT1 and HisACAT2 cells were stored at $5 \times 10^6$ cells/ml in 90% fetal bovine serum and 10% dimethyl sulfoxide at $-80°$ C.

Chinese hamster ovary (CHO) cells were grown as monolayers in medium A (Ham's F-12 supplemented with 10% fetal bovine serum and 10 mg/ml gentamycin) at 37° C. in a 5% $CO_2$ incubator. By using appropriate constructs for transfection into AC29 cells, stable clones were isolated that either expressed the untagged ACAT-1, the His-T7-tagged HisACAT-1, the untagged ACAT-2, or the His-T7-tagged HisACAT-2. Stable transfectant clones were isolated using a procedure described above.

The source of ACAT1 and ACAT2 was recombinant human ACAT1 or recombinant human ACAT2 tagged with His6 at the N-terminus. The enzymes were expressed by Chinese hamster ovary cells and purified using a nickel affinity column as previously described (Chang et al. 2000. *J. Biol. Chem.* 275:28083-28092). Based on specific activity analysis, the ACAT enzymes were purified to an average of 190-fold from crude cell extracts, with approx. 6% recovery of total ACAT activity. After purification, the ACAT1 and ACAT2 preparations were stored in 0.5% CHAPS with 10% DMSO at $-80°$ C. Stored under these conditions, the ACAT activity remained stable for at least one year. Specific activity of 1 unit of ACAT was defined as 1 pmol of cholesteryl oleate formed/minute/µg of protein, assayed under standard mixed micelle conditions.

Example 2

Recombinant ACAT Expression in H293 Cells

Method for Generating the HisACAT1/FLAG Plasmid and Recombinant H293 Cells.

To aid in enzyme purification, a conventional FLAG octapeptide was inserted at the C-terminus of HisACAT1 cDNA (Guo, Z. Y. et al. 2005. *J. Biol. Chem.* 280:37814-37826). This construct (HisACAT1/Flag) was then ligated into the mammalian expression vector pAG3-Zeo (Ikeuchi, T. et al. 2003. *J. Biol. Chem.* 278:7010-7018), using the BamHI and ApaI cloning sites. This plasmid was transfected into HEK293S cells; individual stable clones were isolated by selecting cells resistant to zeocin at 400 µg/mL.

Method for Purifying the HisACAT1/FLAG Protein.

HEK293S cells stably expressing HisACAT1/Flag were seeded in 145 mm dishes for 2-3 days until the cells reached confluency. Cells were rinsed 2× with phosphate-buffered saline (PBS) and harvested by directly solubilizing the cells with buffer A (1 M KCl, 2.5% CHAPS in 50 mM $KH_2PO_4$ buffer at pH 7.8; 1 mL/dish). The detergent-solubilized cell extracts were centrifuged at 100000 g for 1 hour at 4° C.; the solubilized enzyme preparation was loaded onto a mL column containing HIS-BIND resin (Novagen). The column was washed with four column volumes of 20 mM imidazole in buffer B (0.5 M KCl, 0.5% CHAPS in 50 mM $KH_2PO_4$ buffer at pH 7.8). The fusion protein was eluted from the column using two column volumes of 500 mM imidazole in buffer B. The eluate was then applied to a 5 mL FLAG M2 affinity gel and allowed to flow by gravity. After extensive buffer washes using buffer B, the HisACAT1/FLAG fusion protein was eluted from the column with three column volumes of 100 µg/mL FLAG peptide in buffer B. The purified fusion protein was stored at $-80°$ C. for at least 6 months without detectable loss in enzyme activity.

Methods for Determining ACAT Enzyme Activity.

To monitor enzyme activity during enzyme purification, the enzyme solubilized in the detergent CHAPS was assayed in preformed taurocholate/cholesterol/phosphatidylcholine (PC) mixed micelles as described previously (Chang, C. C. et al. 1998. *J. Biol. Chem.* 273:35132-35141), with a final concentration of taurocholate at 9.3 mM, PC at 11.2 mM, and cholesterol at 1.6 mM. The amount of mixed micelle solution was used to dilute the detergent presented in the enzyme preparation, so the final CHAPS/PC molar ratio was less than 0.4. The fatty acyl-CoA substrate saturation curves and cholesterol substrate saturation curves were performed under the same conditions as described previously (Chang, C. C. et al. 1998. supra).

Methods for Measuring Intrinsic Fluorescence.

Fluorescence measurements were generated using an ISS PC1 photocounting fluorescence spectrophotometer (model 90095). This instrument has continuously reproducible slits ranging from 0.4 to 32 nm band-pass. The excitation slit width was set at 2 nm. The wavelength for excitation was set at 295 nm in order to minimize the contribution of tyrosine residues to the fluorescence. Purified HisACAT1/FLAG was concentrated using 30K AMICON centrifugal filters such that the final concentration of the protein was 100-200 ng/µL (1.5-3 µM). Purified protein was stored at $-80°$ C. until used. Unless stated otherwise, the fluorescence measurements were performed at pH 7.8 with 50 mM potassium phosphate, 0.5M KCl, and 8.13 mM CHAPS. Sterol (cholesterol, epicholesterol, coprostanol, and epicoprostanol) was prepared as CHAPS/PC/sterol mixed micelles (with CHAPS at 8.13 mM, PC at 4 mM, and with varying concentrations of sterols as indicated) and stored at 20° C. in the dark until usage. The fatty acyl-CoAs were dissolved in 20 mM sodium acetate at pH 6.4 as a 2 mM stock and stored at −80° C. until used. Before the experiment started, all reagents were kept on ice in the dark. To begin the experiment, 50 μL of mixed micelles without or with sterols was added into a HELLMA microcuvette with 3 mm light path. Twenty-five microliters of ACAT1 protein (in 8.13 mM CHAPS and 0.5 M KCl) was then added and rapidly mixed. Fluorescence was monitored within 15 seconds of adding the enzyme. The sample compartment of the instrument was maintained at 20° C. The fluorescence emission spectrum was scanned in 2 minutes between 310 and 410 nm. The differences in fluorescence intensity at 10 intervals within 325-335 nm were averaged in order to calculate the ΔF value between the ligated protein vs that of the unligated protein.

Gel Electrophoresis and Staining.

Samples were run on 8% SDS-PAGE using conventional methods. The gels were stained with the SILVERQUEST silver staining kit (Invitrogen).

Expression and Purification of Recombinant hACAT1 (HisACAT1/FLAG) in H293 Cells.

H293 cells were transfected with the mammalian expression vector pAG3 that contained the hACAT1 tagged with 6His at the N-terminus and FLAG at the C-terminus (designated as HisACAT1/FLAG) as the insert. Various clones that stably expressed the recombinant protein were then isolated. Western blot analysis was used to monitor the hACAT1 protein expression level. The results showed that the tagged hACAT1, with an apparent molecular mass of 56 kDa in SDS-PAGE, was expressed in H293 cells. H293 cells express (untagged) hACAT1 endogenously, with an apparent molecular mass of 50 kDa. The endogenous hACAT1 could also be detected in the H293 cells that stably expressed HisACAT1/FLAG, especially when a larger amount of cellular protein (50 μg) was employed in the western blot analysis. By comparison, HisACAT1 and untagged hACAT1 stably expressed in CHO cells exhibited an apparent molecular weight of 56 or 50 kDa, respectively. In a separate experiment, ACAT1 expression levels in CHO cells or in H293 cells were monitored with antibodies against ACAT1 or antibodies against FLAG. The results showed that the HisACAT1/FLAG could also be detected by the FLAG antibodies as a broad, 56 kDa protein band. On the basis of the average of several experiments, it was estimated that in H293 cells the HisACAT1/FLAG was expressed at protein levels approximately 20 times as high as the endogenous hACAT1. It has been reported that a relatively high protein expression level of HisACAT1 can be achieved using recombinant baculovirus infection of SF9 cells (Chen, D. et al. 1995. *J. Biol. Chem.* 270:685-695) or H5 cells (Yu, C. et al. 2002. *Biochemistry* 41:3762-3769). Western blot analysis was conducted and the relative ACAT1 protein expression levels in baculovirus infected H5 cells were compared to expression levels in H293 cells stably or transiently expressing HisACAT1/FLAG. The results showed that His ACAT1 expression levels in baculovirus-infected H5 cells and the H293 cells stably expressing the HisACAT1/FLAG were comparable. Additional results showed that in H293 cells the HisACAT1/FLAG expression level was higher in the stable clone than in the cells that are transiently transfected with the HisACAT1/FLAG plasmid.

ACAT-specific enzyme activity in cell homogenates was subsequently compared for CHO cells vs H293 cells. The results (Table 1) showed that the enzyme activity of a stable clone of H293 cells expressing HisACAT1/FLAG was about 9-10 times higher than that of a stable clone of CHO cells either expressing hACAT1 or expressing HisACAT1. The results also showed that the endogenous ACAT activity in the nontransfected H293 cells was less than 5% that of the stable clone expressing HisACAT1/FLAG.

TABLE 1

| Source | ACAT-Specific Activity (pmol min$^{-1}$ mg$^{-1}$) |
| --- | --- |
| AC29 | 0.4 |
| HEK293 | 37.2 |
| hACAT1 in CHO | 131.6 |
| HisACAT1 in CHO | 116.5 |
| HisACAT1/FLAG in HEK293 | 1199 |

Cell extracts were solubilized in 1 M KCl and 2.5% CHAPS and assayed in cholesterol/PC/taurocholate mixed micelles.

Based upon these results, monolayers of H293 cells stably expressing HisACAT1/FLAG were used as a source for purifying the enzyme. To avoid the use of acidic pH conditions during purification, which may cause partial enzyme denaturation, the recombinant hACAT1 construct was designed to further include a FLAG tag at the C-terminus of hACAT1. In this respect, a monoclonal antibody against FLAG was used as the affinity probe in a second column chromatography step. In this manner, the enzyme could be eluted from the column by using an eluting buffer that contained the FLAG peptide at neutral pH. Table 2 summarizes the results of two representative experiments. The total recovery in enzyme units was approximately 7%. The purity of the recombinant hACAT1 was essentially homogeneous, as judged by SDS-PAGE and silver staining.

TABLE 2

| Enzyme Source | % ACAT Enzyme Recovery |
| --- | --- |
| Whole cell extract | 100 |
| Solubilized enzyme | 97 |
| Nickel column chromatography | 21 |
| FLAG column chromatography | 32 |
| Total Recovery | 7 |
| Total ACAT unit | 118 nmol/min |
| Total ACAT1 protein recovered | 250 μg |

Starting material was 55 dishes (145 cm$^2$) of H293 cells stably expressing HisACAT1/FLAG.

Intrinsic Fluorescence of hACAT1.

hACAT1 contains 550 amino acids; 15 of them are tryptophan (W) and 29 are tyrosine residues. To avoid the fluorescence contributed by tyrosine, excitation was set at 295 nm and emission of fluorescence was monitored from 310 to 410 nm. The spectrum was characterized by a single peak centered at 330 nm, due to tryptophan fluorescence of the protein. The effects of pH on ACAT1 fluorescence were tested and the results showed that the fluorescence intensities of the protein gradually increased when the pH values increased from 6 to 9; however, when the pH value increased from 9 to 10, a 24% decrease in fluorescence intensity occurred. It was noted that quenching of the protein fluorescence signal occurred gradually. When measuring samples at 20° C. in the dark and at various pHs (from 6 to 10), approximately 10% of the signal was lost in 15 minutes, presumably due to photobleaching of the protein fluorescence.

The effect of KCl on ACAT1 fluorescence was also determined. The results showed that KCl added at 0.25 M or higher concentrations significantly increased the fluorescence intensities of the protein; at 1 M KCl, the intensity was 2.2-fold higher than the value in the absence of KCl. This observation correlated well with a previous observation that KCl added at 0.5-1 M concentration increased the enzyme activity of the detergent-solubilized ACAT1. Under conditions without or with high KCl, the fluorescence signal gradually decreased, with 8% loss in 5 minutes and 12% in 15 minutes. To minimize quenching in fluorescence intensity, the fluorescence spectrum of the protein was taken rapidly (within 10-15 seconds) after the protein was added to the cuvette that already contained the substrate.

Changes in Intrinsic Fluorescence of hACAT1 Upon Binding to Fatty Acyl-Coenzyme A or Sterol.

Prior to conducting binding experiments, steady-state enzyme kinetic experiments were conducted using purified HisACAT1/FLAG as the enzyme source and either oleoyl-(18:1) CoA or stearoyl- (18:0) CoA as the variable substrate, at a constant, saturating level of cholesterol in the CHAPS/PC mixed micelles. The results showed that the $K_m$ for oleoyl-CoA was 1.3 µM and was 6.4 µM for stearoyl-CoA; the $V_{max}$ value for oleoyl-CoA was 2.4-fold higher than for stearoyl-CoA. These results demonstrated that ACAT1 preferred oleoyl-CoA to stearoyl-CoA as the substrate.

Binding studies were subsequently conducted by monitoring the effect of increasing concentrations of oleoyl-CoA on the intrinsic fluorescence of HisACAT1/FLAG. The results showed that while the peak of the spectrum remained unaltered, the peak height was increased by approximately 32%, with respect to the unliganded ACAT1 protein. A parallel experiment showed that stearoyl-CoA added at increasing concentrations also caused increases in the intrinsic fluorescence of HisACAT1/FLAG. However, the maximal change in the peak of the spectrum was much smaller (5% with respect to the unliganded protein). These results showed that the oleoyl-CoA-induced fluorescence change was specific and saturable. The data was analyzed for a simple bimolecular dissociation equilibrium using the PRISM program. The results showed that the dissociation constant for oleoyl-CoA was 1.9 µM. The changes caused by stearoyl-CoA were too small to derive a reliable dissociation constant.

Steady-state kinetic studies have been conducted and the results demonstrated that cholesterol was an efficient substrate as well as an efficient activator, while epicholesterol (which contains the OH moiety at 3R) or enantiomeric cholesterol (which is the mirror image of cholesterol) was neither a substrate nor an activator for ACAT1. Using the purified HisACAT1/FLAG as the enzyme source, cholesterol substrate saturation curves were determined by varying the cholesterol concentration from 5 to 1600 µM, with oleoyl-CoA concentration kept at 70 µM. The results showed that the shape of the cholesterol saturation curve was sigmoidal.

Binding experiments were subsequently performed by monitoring the effect of increasing concentrations of cholesterol, from 10 to 600 µM, on the intrinsic fluorescence of HisACAT1/FLAG. The results showed that the peak height was positively altered by cholesterol in a concentration-dependent manner, reaching up to 35% with respect to unliganded ACAT1 protein. It was estimated that the cholesterol concentration that caused half-maximal spectral change was 35 µM. A parallel experiment was conducted using epicholesterol as the ligand and it was shown that epicholesterol at similar concentrations examined (from 0.5 to 500 µM) also caused a positive change in the peak height of the spectrum. However, the maximal changes in the peaks of the spectrum caused by epicholesterol, especially at higher sterol concentrations, were much smaller than those caused by cholesterol. Similar to the result obtained when stearoyl-CoA was tested as the ligand, the changes caused by epicholesterol were too small to derive a reliable binding curve. The changes in the intrinsic fluorescence of ACAT1 caused by cholesterol, epicholesterol, coprostanol, or epicoprostanol as the ligand were also compared. The results showed that at 5 or 500 µM, the change caused by cholesterol was much larger than the changes caused by either one of the other three sterols.

Example 3

Assay of Pregnenolone Esterification Activity by ACAT In Vitro

To assay the enzyme, the pregnenolone/detergent/PC micelles and the cholesterol/detergent/PC micelles were prepared individually as follows: the radiolabeled pregnenolone/PC mixture or the cholesterol/PC mixture was prepared as described previously (Shi et al. 1989. *Biochim. Biophys. Acta* 982:187-195) and lyophilized to remove residual organic solvents. After lyophilization, the detergent sodium taurocholate (or other detergent such as CHAPS) in Buffer A was added to reach a final concentration of 10 mg/ml. The mixture was purged with nitrogen, followed by sonication until this mixture was clear. The pregnenolone/PC micelles were mixed with the cholesterol/PC micelles such that the cholesterol concentration is at 0 mM or at 0.32 mM, and the radioactive pregnenolone concentration is at 1 µM (specific activity 20 Ci/mmol). The start the enzyme reaction, 70-100 µl of mixed micelles containing radioactive pregnenolone, with or without cholesterol, and 5 to 10 µl of ACAT1 or ACAT2 (solubilized in the detergent 0.5% CHAPS) were mixed and incubated on ice for 5 minutes. ACAT assay was initiated by adding 20 µl of solution containing 10 nmol of non-radioactive oleoyl-CoA and 10 nmol of fatty acid-free bovine serum albumin to the micelle/enzyme mixture. The reaction mixture was incubated at 37° C. for up to 30 minutes. The reaction was terminated by adding 2:1 chloroform/methanol and the lipids were extracted, separated by thin-layer chromatography. The radioactive pregnenolone ester bands are identified, scrapped, and quantitated by scintillation counting. Other methods for lipid extraction may be employed as can other systems for separating radioactive pregnenolone ester from radioactive pregnenolone.

What is claimed is:

1. A method of identifying an allosteric acyl-coenzyme A: cholesterol acyltransferase (ACAT) inhibitor comprising:
   a) determining, for a candidate compound, a level of inhibition of pregnenolone esterification by ACAT in vitro in the presence of cholesterol;
   b) determining, for the compound, a level of inhibition of pregnenolone esterification by ACAT in vitro without the presence of cholesterol; and
   c) comparing the level of inhibition of pregnenolone esterification in the presence of cholesterol with the level of inhibition of pregnenolone esterification without the presence of cholesterol, wherein the candidate compound is identified as an allosteric ACAT inhibitor if it inhibits pregnenolone esterification by ACAT in the presence of cholesterol but does not inhibit pregnenolone esterification by ACAT without the presence of cholesterol.

2. The method of claim 1, wherein said allosteric ACAT inhibitor is an ACAT1 inhibitor or an ACAT2 inhibitor.

3. The method of claim 1, wherein the esterification of pregnenolone by ACAT in vitro is determined in an assay that comprises a histidine-tagged recombinant human ACAT1 or a histidine-tagged human ACAT2 enzyme.

4. The method of claim 3, wherein the esterification of pregnenolone by ACAT in vitro is tested in a mixed micelle mixture that further comprises a detergent, phosphatidylcholine, a radiolabelled pregnenolone, and fatty acyl-coenzyme A.

5. The method of claim 1, wherein multi-well microtiter plates are used for high throughput screening to identify allosteric ACAT inhibitors.

6. A method of identifying a novel acyl-coenzyme A: cholesterol acyltransferase (ACAT) inhibitor comprising
   determining, for a candidate compound, a level of inhibition of pregnenolone esterification by ACAT in vitro without the presence of cholesterol
   wherein the candidate compound is identified as a novel ACAT inhibitor if it inhibits pregnenolone esterification by ACAT.

7. The method of claim 6, wherein said novel ACAT inhibitor is an ACAT1 inhibitor or an ACAT2 inhibitor.

8. The method of claim 6, wherein the esterification of pregnenolone by ACAT in vitro is determined in an assay that comprises a histidine-tagged recombinant human ACAT1 or a histidine-tagged human ACAT2 enzyme.

9. The method of claim 8, wherein the esterification of pregnenolone by ACAT in vitro is tested in a mixed micelle mixture that further comprises a detergent, phosphatidylcholine, a radiolabelled pregnenolone, and fatty acyl-coenzyme A.

10. The method of claim 6, wherein multi-well microtiter plates are used for high throughput screening to identify novel ACAT inhibitors.

* * * * *